United States Patent [19]  
Gessa et al.

[11] Patent Number: 4,983,632
[45] Date of Patent: Jan. 8, 1991

[54] USE OF GAMMA-HYDROXYBUTYRIC ACID SALTS FOR PREPARING PHARMACEUTICAL COMPOSITIONS FOR USE IN THE TREATMENT OF ALCOHOLISM, AND THE COMPOSITIONS OBTAINED

[75] Inventors: Gian Luigi Gessa; Fabio Fadda, both of Cagliari; Chiara Mormile Di Campochiaro, Sanremo, all of Italy

[73] Assignee: Laboratorio Farmaceutico C.T. S.r.l., Sanremo, Italy

[21] Appl. No.: 361,490

[22] Filed: Jun. 2, 1989

[30] Foreign Application Priority Data

Jun. 3, 1988 [IT] Italy ............................ 20859 A/88

[51] Int. Cl.$^5$ ............................................. A61K 31/19
[52] U.S. Cl. ........................................ 514/557; 514/811
[58] Field of Search ................................. 514/557, 811

[56] References Cited

FOREIGN PATENT DOCUMENTS 044801 1/1982 European Pat. Off. .

OTHER PUBLICATIONS

ZH. Nevropatol. Psikhiatr. (USSR), vol. 66, No. 5,1966, pp. 763–767, V. M. Banstchikov et al.
Farmakol. Toksikol. (USSR), vol. 51, No. 3, May/Jun. 1988, pp. 89–94, R. U. Ostrovskaya et al.
Int. J. Addict., vol. 16, No. 6, Aug. 1981, pp. 1071–1075; Marcel Dekker Inc., M.J.A.J.M. Hoes et al.
Japan. J. Pharmacol., vol. 32, No. 3, 1982, pp. 499–508, Y. Yamanaka.
Farmakol. Toksikol. (MOSCOW), vol. 41, No. 6, 1978, pp. 660–665, L. M. Andrenova et al.
Byull. Eksp. Biol. Med., vol. 91, No. 6, 1981, pp. 689–691, Y. V. Burov et al.
ZH. Nevropatol. Psikhiatr., vol. 81, No. 7, 1981, pp. 1064–1071, A. M. Danilenko et al.
Sov. Med., No. 7, Jul. 1977, pp. 47–51, E. P. Sokoiova et al.
Naunyn-Schmiedeberg's Arch. Pharmacol., vol. 295, No. 3, Dec. 17, 1976, pp. 203–209, Springer-Verlag, De. J. Cott et al.
Dialog Information Services, File 155, Medline, Accession No. 05499632, E. A. Churkin et al. & Sov. Med., 1984 (12), pp. 67–71.
Byull. Eksp. Biol. Med., vol. 95, No. 1, Jan. 1983, pp. 60–62; Yu. V. Burov et al.
Byull. Eksp. Biol. Med. (USSR), vol. 101, No. 2, 1986, pp. 170–172, Yu. V. Burov et al.
Dialog Information Services, file 155, Medline, accession No. 04015342, G. A. Obukhov and ZH. Nevropatol. Psikiatr. 1980 (1), pp. 130–131.

Primary Examiner—Stanley J. Friedman
Attorney, Agent, or Firm—Birch, Stewart, Kolasch & Birch

[57] ABSTRACT

The use of gamma-hydroxybutyric acid salts for preparing pharmaceutical compositions useful for the release form ethyl alcohol consumption and the compostions obtained.

10 Claims, No Drawings

4,983,632

USE OF GAMMA-HYDROXYBUTYRIC ACID SALTS FOR PREPARING PHARMACEUTICAL COMPOSITIONS FOR USE IN THE TREATMENT OF ALCOHOLISM, AND THE COMPOSITIONS OBTAINED

FIELD OF THE INVENTION

This invention relates to the use of gamma-hydroxybutyric acid salts for preparing pharmaceutical compositions for use in the treatment of alcoholism, and the compositions obtained; the expression "treatment of alcoholism" signifying release from the habit of consuming drinks containing ethyl alcohol and treatment of ethyl alcohol dependence.

More particularly, the invention relates to the use of an organic or inorganic salt of gamma-hydroxybutyric acid for preparing pharmaceutical compositions suitable for oral or parenteral administration in the treatment of alcoholism. The following abbreviations are used in the present text: GHB=gamma-hydroxybutyric acid, NaGHB=sodium salt of gamma-hydroxybutyric acid, ADH=alcohol dehydrogenase, ALDH=aldehyde dehydrogenase, M.S.E.=mean standard error, O.D./min/mg prot.=optical density/minute/mg of protein, C.L.=95% confidence limit.

TECHNICAL PROBLEM

In industrial countries alcohol has the peculiarity of being the only pharmacological agent able to produce socially accepted self-intoxication, alcoholism being by far the most serious social problem in all industrialised countries, discounting cigarettes.

When measured in terms of accidents, productivity breakdown, crime, death or illness, the social cost of this problem is incalculable, as is the cost in terms of families ruined, lives lost, loss to society and human tragedy.

Ethyl alcohol dependence arises when an individual's alcohol consumption exceeds customarily acceptable limits or is such as to damage his health or hinder his social relationships. Psychic alcohol dependence exists at all levels. At the lowest levels alcohol is sought, or its need is felt, both as a food and as a means for social relationship. A moderate degree of psychic dependence arises when an individual feels the need to drink in order to work or to participate in social life, and he tends to increase its consumption to attain these ends. Strong dependence arises when an individual consumes more alcohol than the usual socio-cultural norms allow, drinks in situations within which one does not normally drink, and feels urged to drink alcohol contained in toxic liquids which are not normally used as drinks.

Continuous alcohol consumption results in a slight but definite increase in the quantity of alcohol required to maintain a determined alcohol level. A physiological and psychological adaptation also occurs such that the alcoholic appears less intoxicated and less influenced in performance tests for a certain alcohol concentration in the blood compared with when he did not drink.

The physical dependence on alcohol and the abstinence syndrome manifest themselves when the alcohol consumption is reduced below the critical level. The damage caused to the individual by alcohol dependence can be quantitatively greater than that caused by any other type of dependence. Alcohol alters the intellectual faculty and psychomotor coordination, to determine a deterioration in working capacity. Deterioration in judgement can lead to all manner of business errors and disturb relationships with other people. Conscious behaviour control disappears, with resultant exhibitionism and aggressiveness, and in addition alcohol dependence also predisposes and leads to serious indirect physical disturbances by neglect of hygiene, or by inadeguate diet with consequent vitamin, protein and mineral salt deficiency.

The most serious complication of alcoholism is hepatic cirrhosis.

PRIOR ART

The most widely used substance in the treatment of chronic alcoholism is disulfiram (Antabuse). This treatment is based on the observation that a subject treated with disulfiram shows very unpleasant and clinically objectionable symptoms when he imbibes alcohol.

Disulfiram in itself is not toxic, although not completely innocuous, when administered alone in therapeutic doses. However disulfiram considerably alters alcohol metabolism with the result that when alcohol is administered to an animal or an individual who has previously been treated with disulfiram, the acetaldehyde level in the blood is 5-10 times greater than that present in the animal or individual when treated only with the same dose of alcohol. This effect is accompanied by signs and symptoms known as the "acetaldehyde syndrome" or "disulfiram alcohol reaction", and it has been established that most of these dramatic symptoms observed after ingesting disulfiram and alcohol are due to an increase in the hematic acetaldehyde in that these signs have also been observed after intravenous administration of acetaldehyde.

Acetaldehyde is produced by the initial oxidation of alcohol by the liver alcohol dehydrogenase. It does not normally accumulate in the tissues as it is gradually oxidised by the aldehyde-dehydrogenase enzyme when formed. In the presence of disulfiram the acetaldehyde concentration increases assumedly because the disulfiram competes with the nicotine-adenine dinucleotide (NAD) on the active sites of the aldehyde-dehydrogenase enzyme, thus reducing the acetaldehyde oxidation rate.

Patients treated with this substance refuse alcoholic drinks to avoid the unpleasant toxic and sometimes fatal effects due to the accumulation of acetaldehyde (Goodman and Gilman, Le basi farmacologiche della terapia, p. 408, 1982).

Finally, disulfiram is itself not completely innocuous and can cause acneform eruptions, allergic dermatitis, urticaria, tiredness, fatique, tremors, reduced sexual power, gastric disturbances and digestive disturbances, and as an aspecific enzymatic inhibitor can also alter the activity of all those enzymes comprising a —SH group as their active site, thus being the cause of further organism damage.

These effects are however not great compared with the much more serious symptoms deriving from the ingestion of even small doses of alcohol by subjects treated with disulfiram. Following disulfiram treatment, cases of respiratory depression, cardiovascular collapse, cardiac arrhythmia, myocardium infarct, and sudden or unexpected death have occurred (F, Lodi, E. Marozzi, Tossicologia forense e chimica tossicologica p. 315, 1982). The use of disulfiram as a therapeutic agent is therefore obviously not without danger, and its use must be under strict medical control. The patient must be told that during disulfiram treatment the cunsumption of alcohol in any form can be lethal, and he must be made aware that alcohol can be present in sauces, fermented drinks, syrups, aftershave lotions etc. The risks of using such a substance for treatment are therefore obvious.

A further series of compounds which have shown some use in the treatment of alcoholism are the a-amino-gamma-butyrolactone derivatives in accordance with the published Italian patent application No. 19390 A/84, filed on Feb. 2, 1984 in the name of the same assignee, which however was subsequently abandoned as these proved less effective in the treatment of alcoholism than the new compounds of the present invention.

SUMMARY OF THE INVENTION

We have now surprisingly found that gamma-hydroxy butyric acid salts are effective in treating alcoholism and alcohol-dependence.

Gamma-hydroxy butyric acid is a normal constituent of the central nervous system of mammals, from which it is extracted in quantity from the mesencephalon and hippocampus, where numerous neurophysiological functions are performed. It is also easily prepared synthetically.

Gamma-hydroxy butyric acid derivatives, which include its simple salts, are substances already known for certain therapeutic uses due for example to their narcotic, hypnotic or anticonvulsive effect, but up to the present time no pharmacological activity usable in the treatment of alcoholism has been described for these substances.

The present invention therefore relates to the use of organic and inorganic salts of gamma-hydroxy-butyric acid in the treatment of alcoholism.

We have found that the GHB salts according to the present invention surprisingly suppress the desire to drink alcohol in laboratory animals and in man without demonstrating any type of toxic effect, in contrast to disulfiram and aldehyde dehydrogenase inhibitors.

We have also found that GHB salts in vitro have no effect on the enzymatic kinetics of this enzyme, and are considerably more effective than α-amino-gamma-butyrolactone derivatives, which have shown considerably less activity for this therapeutic use. Table 1 shows the inhibition of voluntary ethanol consumption by alcohol-preferring rats following treatment with α-n-butyl carbonylamino-gamma-butyro lactone indicated by the code PTT-01

TABLE 1

| PTT-01 (Mg/kg) | Ethanol consumption (g/kg) | | |
|---|---|---|---|
| | Pretreatment | Treatment | Post-treatment |
| vehicle alone | 7.88 ± 0.14 | 7.72 ± 0.19 | 7.68 ±0 M.S.E. 0.23 |
| 100 | 7.21 ± 0.40 | 7.03 ± 0.38 | 7.24 ± 0.44 |
| 200 | 7.70 ± 0.28 | 7.51 ± 0.41 | 7.36 ± 0.51 |
| 300 | 7.08 ± 0.19 | 7.00 ± 0.46 | 6.98 ± 0.15 |

Each value represents the mean of 10 aminals.

To demonstrate the effectiveness of the pharmaceutical compositions of the present invention, experimental trials were carried out, as described hereinafter, on a population of rats chosen for their alcohol-preference.

EFFECT OF GAMMA-HYDROXY BUTYRIC ACID, SODIUM SALT ON THE VOLUNTARY CONSUMPTION OF ETHANOL IN ALCOHOL-PREFERRING RATS

The trial was carried out on male Wistar rats of initial weight 130–160 g. The alcohol-preferring rats were chosen from a heterogeneous rat population having an average age of 40 days. The animals were caged individually and kept in an environment at a temperature of 24° C., with light from 8.00 to 20.00 hous. The method used to select alcohol-preferring rats was to allow the animals to choose from two bottles, one containing water and the other containing an increasingly strong ethanol solution. The tapwater and the ethanol solution were administered from graduated bottles (Richter), their positon being changed irregularly to prevent the habit of drinking from the same bottle. Starting from a 3% ethanol solution, the concentration was increased by 1% every day to a maximum of 10%. This ethanol concentration was used for the whole trial period. The experiments were carried out only on rats by whom more than 60% of the liquid drunk had been 10% ethanol. The thus chosen rats imbibed a constant mean ethanol quantity of 3.2±0.4 g/rat/day. The weight of the animals during this period was 380±35 g, and therefore the consumption of absolute alcohol per rat per kg of body weight was 8±0.54 g.

Different randomly chosen groups of these animals were respectively treated with increasing doses of the sodium salt of gamma-hydroxy butyric acid (NaGHB) wheas the control group received the same volume of physiological solution (10 ml/kg). The quantity of ethanol and water imbibed was recorded before, during and after treatment at the same time each day, and the treatment was repeated for three consecutive days.

Alcohol consumption and preference for alcohol returned to their pre-treatment levels five days after interrupting the administration of the medicament. It should also be noted that during treatment with NaGHB there was no significant reduction in total imbibed fluid.

The results of this trial are given in Table 2 which compares ethanol consumption in g/kg before, during and after treatment with NaGHB at three different doses of 150, 300 and 450 mg/kg. These results are compared with those for an untreated control.

TABLE 2

| NaGHB (mg/kg) | Ethanol consumption (g/kg) | | |
|---|---|---|---|
| | Pretreatment | Treatment | Post-treatment |
| — | 8.09 ± 0.68 | 7.78 ± 0.41 | 7.56 ± 0.34 |
| 150 | 7.71 ± 0.51 | 6.11 ± 0.21 | 7.02 ± 0.44 |
| 300 | 7.48 ± 0.35 | 3.43 ± 0.23 | 5.88 ± 0.35 |
| 450 | 7.82 ± 0.46 | 2.12 ± 0.11 | 5.10 ± 0.48 |

The reduction in alcohol consumption in alcohol-dependent animals is not caused by inhibition of the ethanol metabolizing enzymes, and in fact up to a concentration of $10^{-3}$M the NaGHB does not inhibit alcohol dehydrogenase (ADH) or the aldehyde dehydrogenase (ALDH). The ADH and ALDH activity were measured using the surnatant of rat liver homogenate. The ADH activity was measured by oxidising the ethanol to acetaldehyde in the presence of NAD in tubes containing NaGHB.

The formation of reduced nicotine-adenine dinucleotide (NADH) was determined by spectrometry measurement at 340 nm and the ALDH activity was determined in the same manner. In addition, pyrazole (0.03M) was added to the reaction mixture to inhibit ADH and propionaldehyde was added as substrate. Each value is the mean±M.S.E. of three experiments. The results are given in Table 3.

TABLE 3

| Molar concentration | ADH activity | ALDH activity |
|---|---|---|
| | D.O/min/mg prot | |
| nome | 0.0235 ± 0.0012 | 0.0141 ± 0.0013 |
| NaGHB $10^{-5}$ | 0.0245 ± 0.0018 | 0.0135 ± 0.0010 |
| NaGHB $10^{-4}$ | 0.0240 ± 0.0018 | 0.0138 ± 0.0011 |
| NaGHB $10^{-3}$ | 0.0239 ± 0.0015 | 0.0132 ± 0.0009 |

The results obtained show that daily administration of NaGHB reduces the consumption of ethyl alcohol to below 50% of the consumption before treatment with NaGHB for administration of 450 mg/kg, without in any way altering acetaldehyde metabolism and thus without causing the dangerous "acetaldehyde syndrome". In addition, acute or chronic toxicity of gamma-hydroxy butyric acid or its salts is completely absent.

An acute toxicity test was conducted on the mouse, giving $LD_{50}$ values for NaGHB of 12.014 g/kg and 3.21 g/kg for oral administration (Table 4) and intraperitoneal administration (Table 5) respectively.

TABLE 4

ACUTE TOXICITY FOR ORAL ADMINISTRATION IN THE MOUSE

| Treatment | Dose (g/kg) act. princip) | No. animals treated | dead | tality (M+F) | $LD_{50}$ (95%CL) (mg/kg) |
|---|---|---|---|---|---|
| NaGHB | 15 | 6M + 6F | 6M + 6F | 100 | |
| NaGHB | 13 | 6M + 6F | 4M + 4F | 66.6 | 12.014 |
| NaGHB | 11 | 6M + 6F | 2M + 2F | 33.3 | |
| NaGHB | 10 | 6M + 6F | — | 0 | (10.95–13.17) |

TABLE 5

ACUTE TOXICITY FOR INTRAPERITONEAL ADMINISTRATION IN THE MOUSE

| Treatment | Dose (g)kg act. princip.) | No. animals treated | dead | Mortality (M + F) | $LD_{50}$ (95%CL) (mg/kg) |
|---|---|---|---|---|---|
| NaGHB | 4 | 6M + 6F | 6M + 6F | 100 | |
| NaGHB | 3.5 | 6M + 6F | 4M + 4F | 66.7 | 3.21 |
| NaGHB | 3 | 6M + 6F | 2M + 2F | 33.3 | |
| NaGHB | 2.5 | 6M + 6F | — | 0 | (2.92–3.521) |

No toxic action at organ level was observed during chronic toxicity tests on the rat.

To the end of demostrating the efficacy of the pharmaceutical compositions according to the invention we have furthermore carried out some chemical tests to evaluate the efficacy of GHB salts in obtaining and mantaining abstention from alcoholic drinks in man; we synthetically report herein below the methods followed and the results obtained in one of such studies.

EFFECT OF GHB ACID SODIUM SALTS ON VOLUNTARY CONSUMPTION OF ETHYL ALCOHOL BY MAN

Chemical Study 1

One must first of all have an instrument to distinguish between the craving for drinks of alcoholics and the one of non-alcoholics.

Drinking is in fact an extremely variable "life style", in dependence of the individuals counsidered.

To this end we have prepared a questionnaire entitled "Restrained Drinking and Alcohol Craving Scale" (RDAGS) and we have examined whether said questionnaire was capable of differentiating between alcoholics and non-alcoholics.

The test consisted in comparing 40 alcoholic subjects with 40 non-alcoholic subjects assorted with the first in relation to age, sex and civil status variables.

We than proceeded in calculating the average scores±50 for the two groups. A correlational analysis of each item of the questionnaire on the total score was then carried out, which allowed to answer the two following fundamental questions:

1. The frequency of each item in comparison with normal answers, that is the capacity of each item to describe its own characteristics;

2. The correlation existing between the various items and the total score, in order to evaluate the variance.

These experiments allowed us to conclude that the devised instrument was reliable for distinguishing the craving for drinks typical of alcoholics from the one typical for normal drinkers.

We have then established, through the test-retest reliability technique, that the craving for drinks containing ethyl alcohol is stable, that is it remains constant in the natural history of the patient without undergoing spontaneous changes.

Finally, to the end of proving that the craving for drinks containing ethyl alcohol ("craving" for short) can be modified by pharmacological treatment with the compositions according to the present invention, we have selected 40 alcohol-dependent individuals according to the Diagnostic and Statistic Manual, 3rd edition Revised (DMS-III R) classification.

To more individuals a NaGHB treatment at the doses of 0.05 g/kg/day in two administrations was given for an average period of 4–6 weeks.

For comparison, a group of 40 alcoholics was examined, using the same criteria as for the NaGHB treatment groups; to this group a psychological and/or socio-rehabilitation technique was applied, with no specific pharmacological support (polyvitamins only).

The results obtained have allowed us to establish that following the NaGHB treatment there is a statistically highly significant craving reduction.

In order to obtain a further experimental confirmation of the results obtained in the open test, we have carried out a test in double-blind.

80 individuals, alcohol dependent according to DSM III-R, were divided in two groups by simple randomization and treated with NaGHB or with a placebo at the doses of 0.05 g/kg/day divided in two administrations for a total of 60 days.

The NaGHB treated individuals evidenced a notable improvement of the craving with respect to the individuals treated only with placebo, and a lower, statistically significant, drop-out percentage.

The results obtained in this series of tests are summarised in Table 6.

TABLE 6

| Purpose of the test Validation of the R.D.A.C.S. test | Method employed | Results |
|---|---|---|
| 1. Capacity of the test to distinguish between normal drinkers and alcoholics | Administration to 80 individuals: 40 normal drinkers and 40 alcholics | Discriminating |
| 2. Item stability with time in the absence of treatment | Test and re-test after 10 days to 40 individuals (20 + 20) | Stable |
| Craving decrease induced by NaGHB | 40 alcohol-dependents in open test | Efficient |
| | 40 alcohol dependents in double blind test | Efficient |

The results obtained through this clinical study show the surprising activity of GHB in suppressing the craving for ethyl alcohol in alcoholics.

In conclusion, the use of GHB salts in the treatment of alcoholism has proved the most effective treatment with the least absolute toxicity when compared with all treatments known up to the present time.

The composition containing a GHB salt and suitable pharmaceutically acceptable excipients can be formed using various gamma-hydroxy butyric acid salts and excipients. It can also be used in various formulations suitable for oral or parenteral administration according to the particular requirements of the application.

Suitable gamma-hydroxy butyric acid salts include the sodium salt, potassium salt, calcium salt and magnesium salt. In addition to GHB salts, the composition of the present invention can contain one or more non-toxic pharmaceutically acceptable excipients.

The choice of excipient depends not only on the chemical and physical characteristics of the active principle and the required posology, but also on the type of composition desired. The dosage of individual components of the administration obviously varies in accordance with the body weight of the patient and his clinical condition.

The typical dosage for a GHB salt is from 0.025 to 0.10 g/kg, the preferred GHB salt dosage being 0.05 g/kg in a single daily dose.

The GHB salt content of the compositions according to the present invention can vary from 12.5 to 50% by weight.

Compositions according to the present invention suitable for oral or parenteral administration are preferably prepared in the form of syrup, effervescent tablets, sachets containing effervescent powder, fuits jellies or injectable vials.

The following examples of the preparation of compositions according to the present invention are given hereinafter by way of non-limiting illustration only.

EXAMPLE 1

Syrup Bottle Containing 140 ml of Solution

| | |
|---|---|
| Gamma-hydroxy butyric acid, sodium salt, | 42.35 g |
| equivalent to gamma-hydroxy butyric acid | 35.00 g |
| Ammonium glycyrrhizinate | 1.00 g |
| Sodium saccharin | 0.50 g |
| Methyl paraoxybenzoate | 100.00 mg |
| Propyl paraoxybenzoate | 30.00 mg |
| Saccharose | 100.00 g |
| M.U. AK 353 flavouring | 0.50 ml |
| Purified water to make up to | 140.00 ml |

EXAMPLE 2

Bottle Containing 20 ml of Solution

| | |
|---|---|
| Gamma-hydroxy butyric acid, sodium salt | 6.05 g |
| equivalent to: gamma-hydroxy butyric acid | 5.00 g |
| Ammonium glycyrrhizinate | 142.90 mg |
| Sodium saccharin | 71.40 mg |
| Methyl paraoxybenzoate | 14.30 g |
| Propyl paraoxybenzoate | 4.30 mg |
| Saccharose | 14.30 g |
| M.U. AK 353 flavouring | 0.07 ml |
| Purified water to make up to | 20.00 ml |

EXAMPLE 3

Effervescent Tablet

| | |
|---|---|
| Gamma-hydroxy butyric acid, sodium salt, | 3.025 g |
| equivalent to gamma-hydroxy butyric acid | 2.500 g |
| Citric acid | 300 g |
| Sodium bicarbonate | 600 mg |
| Gesilite | 50 mg |
| Microcrystalline cellulose | 400 mg |
| Magnesium stearate | 20 mg |

EXAMPLE 4

Contents of an Effervescent Sachet

| | |
|---|---|
| Gamma-hydroxy butyric acid, sodium salt, | 6.05 g |
| equivalent to gamma-hydroxy butyric acid | 5.00 g |
| Lyophilized orange juice | 1.00 g |
| Orange flavouring | 100 mg |
| Sodium saccharin | 20 mg |
| Saccharose | 10.00 g |

EXAMPLE 5

Composition per 100 g of Jelly

| | |
|---|---|
| Gamma-hydroxy butyric acid, sodium salt, | 30.25 g |
| equivalent to gamma-hydroxy butyric acid | 25.00 g |
| Saccharose | 28.00 g |
| Carob gum | 0.40 g |
| Calcium carrageenate | 0.28 g |
| Tryptophan citrate | 0.16 g |
| Cherry flavouring | 0.16 g |
| Purified water | 40.75 g |

| | |
|---|---|
| Gamma-hydroxy butyric acid sodium salt | 2 g |
| Water for injectable preparations to make up to | 10 ml |

We claim:

1. A method of treating ethyl alcohol dependency in a patient, which comprises:
   administering to said patient an effective amount of a pharmaceutically acceptable salt of gamma-hydroxy butyric acid for treating said dependency.

2. The method of claim 1, wherein said pharmaceutically acceptable salt of gamma-hydroxy butyric acid is the sodium, potassium, calcium or magnesium salt thereof.

3. The method of claim 1, wherein said pharmaceutically acceptable salt of gamma-hydroxy butyric acid is the sodium salt thereof.

4. The method of claim 1, wherein the effective amount of the pharmaceutically acceptable salt of gamma-hydroxy butyric acid for treating said dependency is administered once a day.

5. The method of claim 1, wherein the effective amount of said pharmaceutically acceptable salt which is administered for treating said dependency is from 0.025 to 0.10 g/kg of the patient's weight.

6. The method of claim 4, wherein the effective amount of said pharmaceutically acceptable salt which is administered is from 0.025 to 0.10 g/kg of the patient's weight.

7. The method of claim 6, wherein said pharmaceutically acceptable salt is the sodium, potassium, calcium or magnesium salt of gamma-hydroxy butyric acid.

8. The method of claim 6, wherein said pharmaceutically acceptable salt is the sodium salt of gamma-hydroxy butyric acid.

9. A method of treating ethyl alcohol dependency in a patient, which comprises:
administering to said patient once a day from 0.025 to 0.10 g/kg of the patient's weight, of a pharmaceutically acceptable salt of gamma-hydroxy butyric acid, which is selected from the group consisting of:
the sodium salt of gamma-hydroxy butyric acid,
the potassium salt of gamma-hydroxy butyric acid,
the calcium salt of gamma-hydroxy butyric acid, and
the magnesium salt of gamma-hydroxy butyric acid.

10. The method of claim 9, wherein said pharmaceutically acceptable salt of gamma-hydroxy butyric acid is the sodium salt thereof.

* * * * *